(12) United States Patent
Carmeli et al.

(10) Patent No.: US 11,083,908 B2
(45) Date of Patent: Aug. 10, 2021

(54) ENHANCING EPITHELIAL INTEGRITY BY A SEQUENCE OF MAGNETIC PULSES

(71) Applicant: EPITECH MAG LTD., Yokneam Illit (IL)

(72) Inventors: Tomer Carmeli, Alonei Abba (IL); Ifat Sher-Rosenthal, Shoham (IL); Ygal Rotenstreich, Kfar Bilu (IL); Itzik Ronen, Nirit (IL)

(73) Assignee: EPITECH MAG LTD., Yokneam Illit (IL)

( * ) Notice: Subject to any disclaimer, the term of this patent is extended or adjusted under 35 U.S.C. 154(b) by 150 days.

(21) Appl. No.: 16/039,659

(22) Filed: Jul. 19, 2018

(65) Prior Publication Data
US 2019/0046810 A1 Feb. 14, 2019

Related U.S. Application Data

(63) Continuation-in-part of application No. PCT/IL2016/051392, filed on Dec. 28, 2016.

(30) Foreign Application Priority Data

Jan. 19, 2016 (IL) .......................................... 243686

(51) Int. Cl.
*A61N 2/00* (2006.01)
*A61N 2/02* (2006.01)
(Continued)

(52) U.S. Cl.
CPC ................ *A61N 2/006* (2013.01); *A61F 9/00* (2013.01); *A61F 9/0079* (2013.01); *A61N 2/02* (2013.01)

(58) Field of Classification Search
CPC ...... A61N 2/006; A61N 2/02; A61N 1/36046; A61F 9/00; A61F 9/0079; A61F 9/007
See application file for complete search history.

(56) References Cited

U.S. PATENT DOCUMENTS 5,055,627 A   10/1991 Smith, Jr. et al.
5,135,466 A    8/1992 Fedorov et al.
(Continued)

FOREIGN PATENT DOCUMENTS

CN   203276182 U   11/2013
GB     2271931 A    5/1994
(Continued)

OTHER PUBLICATIONS

Extended European Search Report for Application No. 16886201.9, dated Aug. 2, 2019, 9 pages.
(Continued)

*Primary Examiner* — Kaylee R Wilson
(74) *Attorney, Agent, or Firm* — Sughrue Mion, PLLC

(57) ABSTRACT

The invention provides a method of noninvasively treating a condition associated with reduced integrity or increased permeability of an epithelial layer by a series of magnetic pulses having a magnitude of up to 3 T, wherein the magnetic pulses are designed to induce an electric field having a magnitude of up to 250 Volt per meter adjacent to a target treatment area, the condition particularly being ocular condition associated with reduced barrier function of the cornea. The invention provides a device for effecting the tissue treatment, creating series of pulses exhibiting a rate of change of more than 200 T/s in the absolute value.

10 Claims, 4 Drawing Sheets

(51) Int. Cl.
*A61F 9/00* (2006.01)
*A61F 9/007* (2006.01)

(56) References Cited

U.S. PATENT DOCUMENTS

| | | | |
|---|---|---|---|
| 5,725,471 | A | 3/1998 | Davey et al. |
| 7,335,156 | B2 | 2/2008 | Pattern et al. |
| 9,427,224 | B1 | 8/2016 | Jeyanandarajan |
| 2004/0138516 | A1 | 7/2004 | Osorio et al. |
| 2006/0094924 | A1 | 5/2006 | Riehl |
| 2007/0073096 | A1 | 3/2007 | Alvarado |
| 2008/0004484 | A1 | 1/2008 | Wieraszko et al. |
| 2008/0275289 | A1 | 11/2008 | Olree et al. |
| 2010/0249488 | A1 | 9/2010 | Kardos et al. |
| 2010/0324642 | A1 | 12/2010 | Pettinelli |
| 2011/0112427 | A1 | 5/2011 | Phillips et al. |
| 2012/0130398 | A1 | 5/2012 | Ackermann et al. |
| 2013/0123764 | A1 | 5/2013 | Zarsky et al. |
| 2013/0137918 | A1 | 5/2013 | Phillips et al. |
| 2013/0278898 | A1* | 10/2013 | Kato ............ A61B 3/117 351/208 |
| 2014/0257433 | A1 | 9/2014 | Ackermann et al. |
| 2014/0275718 | A1 | 9/2014 | Huang et al. |
| 2014/0316310 | A1 | 10/2014 | Ackermann et al. |
| 2014/0343349 | A1 | 11/2014 | Borsody |
| 2015/0025297 | A1 | 1/2015 | Pan et al. |
| 2015/0100001 | A1 | 4/2015 | Bujak |
| 2015/0328477 | A1 | 11/2015 | Gale et al. |
| 2016/0008620 | A1 | 1/2016 | Stubbeman |
| 2016/0015995 | A1 | 1/2016 | Leung et al. |
| 2016/0022992 | A1 | 1/2016 | Franke et al. |
| 2016/0106996 | A1 | 4/2016 | Sher-Rosenthal et al. |
| 2016/0158562 | A1 | 6/2016 | Bornzin et al. |
| 2016/0367806 | A1 | 12/2016 | Kahook |
| 2017/0333249 | A1 | 11/2017 | Herchman, Jr. et al. |
| 2017/0354818 | A1 | 12/2017 | De Toni et al. |
| 2018/0161579 | A1 | 6/2018 | Franke et al. |
| 2018/0256906 | A1 | 9/2018 | Pivonka et al. |

FOREIGN PATENT DOCUMENTS

| | | |
|---|---|---|
| JP | 2005334586 A | 12/2005 |
| KR | 101134657 B1 | 4/2012 |
| KR | 20180004669 A | 1/2018 |
| RU | 2368405 C1 | 9/2009 |
| RU | 2011114847 A | 4/2011 |
| RU | 2499614 C1 | 11/2013 |
| RU | 2581495 C1 | 4/2016 |
| SU | 1076126 A | 4/1982 |
| WO | 9919020 A1 | 4/1999 |
| WO | 0178829 A2 | 10/2001 |
| WO | 2005105013 A2 | 11/2005 |
| WO | 2009011529 A2 | 1/2009 |
| WO | 2013073840 A1 | 5/2013 |
| WO | 2014181327 A1 | 11/2014 |
| WO | WO-2014181327 A1 * | 11/2014 ............ A61N 2/02 |
| WO | 2015034154 A1 | 3/2015 |
| WO | 2017081087 A1 | 5/2017 |
| WO | 2017208168 A3 | 12/2017 |
| WO | 2018018724 A1 | 2/2018 |

OTHER PUBLICATIONS

The Magstim Company Ltd., "Magstim® Rapid2P/N 3576-23-09 Operating Manual", Nov. 2009, 61 pages.

Lopez-Boado et al., "Macrolides as immunomodulatory medications for the therapy of chronic lung disease", Current Opinion in Pharmacology, 2008, www.sciencedirect.com, pp. 286-291.

Okano et al., "Biphasic Effects of Static Magnetic Fields on Cutaneous Microcirculation in Rabbits", Bioelectromagnetics 20, 1999, pp. 161-171.

MacCabee et al., "Stimulation of the Human Nervous System Using the Magnetic Coil", Journal of Clinical Neurophysiology, vol. 8, No. 1, 1991, pp. 38-55.

Wang et al., "Reduced Innervation and Delayed Re-Innervation After Epithelial Wounding in Type 2 Diabetic Goto-Kakizaki Rats", The American Journal of Pathology, vol. 181, No. 6, Dec. 2012, pp. 2058-2066.

Yang et al., "Substance P Promotes Diabetic Corneal Epithelial Wound Healing Through Molecular Mechanisms Mediated via the Neurokinin-1 Receptor", Diabetes, vol. 63, Dec. 2014, pp. 4262-4274.

Beuerman et al., "Sensory Denervation of the Rabbit Cornea Affects Epithelial Properties", Experimental Neurology, 69, 1980, pp. 196-201.

Nagano et al., "Effects of Substance P and IGF-1 in Corneal Epithelial Barrier Function and Wound Healing in a Rat Model of Neurotrophic Keratopathy", Investigative Opthalmology & Visual Science, Sep. 2003, vol. 44, No. 9, pp. 3810-3815.

Oswald et al., "Communcation between Corneal Epithelial Cells and Trigeminal Neurons Is Facilitated by Purinergic (P2) and Glutamatergic Receptors", PLOS ONE, Sep. 2012, vol. 7, Issue 9, 15 pages.

Toshida et al., "Evaluation of Novel Dry Eye Model: Preganglionic Parasympathetic Denervation in Rabbit", Investigative Opthalmology & Visual Science, Oct. 2007, vol. 48, No. 10, pp. 4468-4475.

Araki-Sasaki et al., "Substance P-Induced Cadherin Expression and Its Signal Transduction in a Cloned Human Corneal Epithelial Cell Line", Journal of Cellular Physiology, 2000, pp. 189-195.

Reid et al., "Stimulation of Epithelial Cell Growth by the Neuropeptide Substance P", Journal of Cellular Biochemistry, 52, 1993, pp. 476-485.

Garcia-Hirschfeld et al., "Neurotrophic Influences on Corneal Epithelial Cells", Exp. Eye Res., 1994, 59, pp. 597-605.

Yamada et al., "Functional genomics and depression research Beyond the monoamine hypothesis", European Neuropsychopharmacology, 12, 2002, pp. 235-244.

* cited by examiner

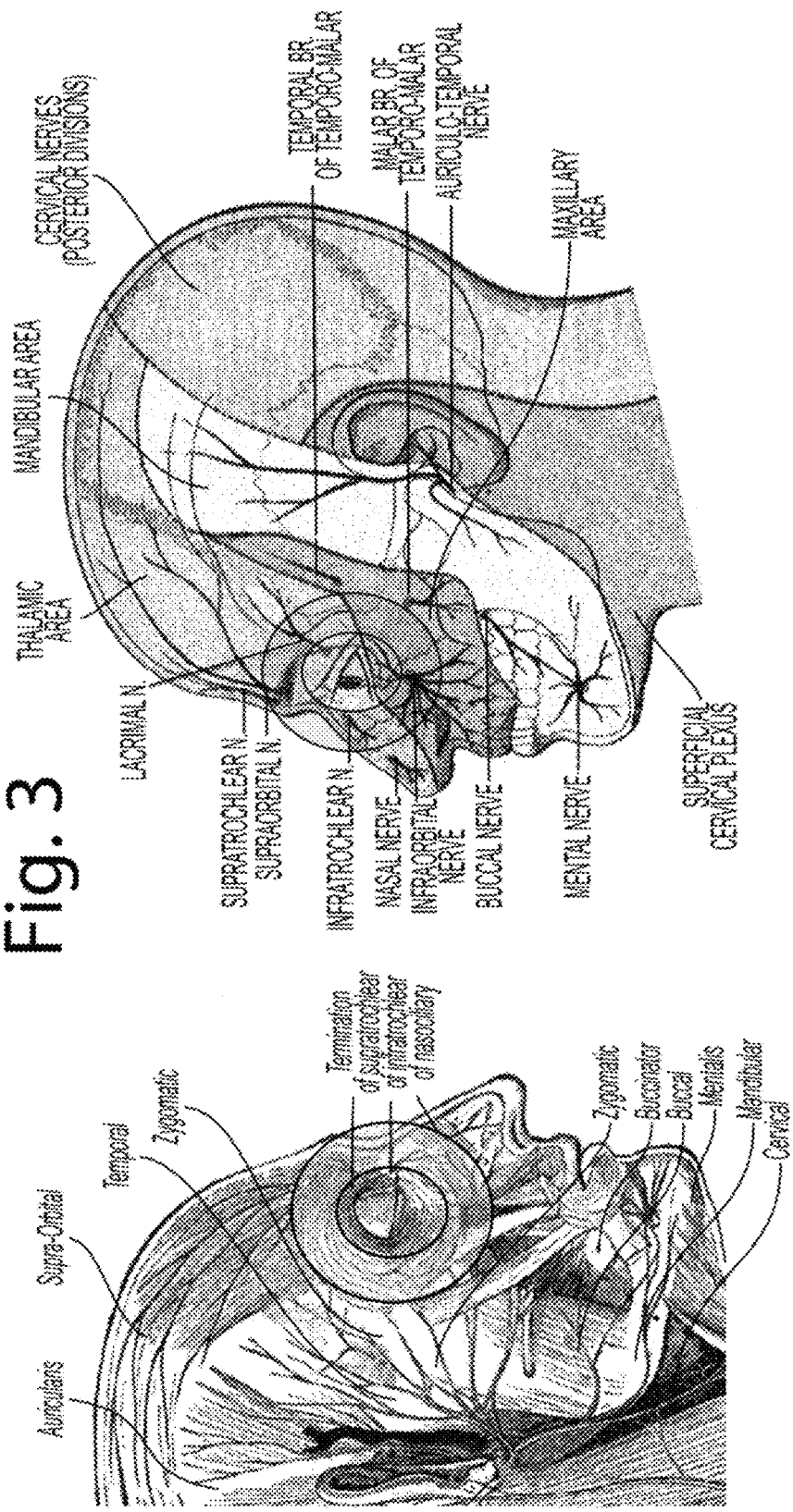

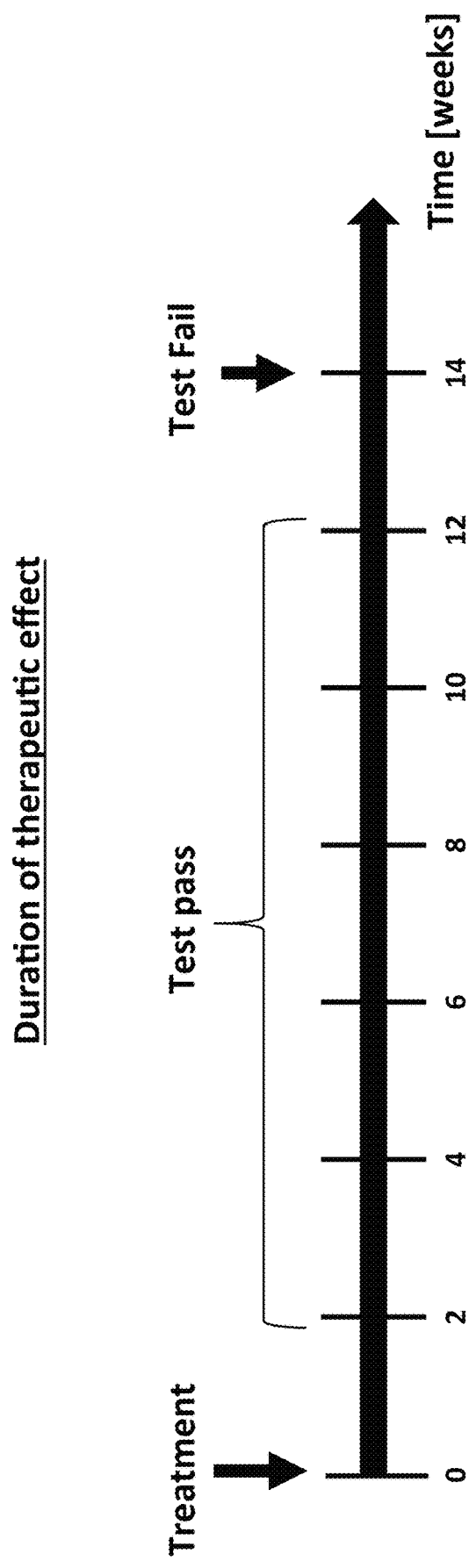

ENHANCING EPITHELIAL INTEGRITY BY A SEQUENCE OF MAGNETIC PULSES

CROSS REFERENCE TO RELATED APPLICATIONS

This application is a continuation-in-part of International Application No. PCT/IL2016/051392, filed 28 Dec. 2016, entitled "ENHANCING EPITHELIAL INTEGRITY BY A SEQUENCE OF MAGNETIC PULSES", which claims priority to Israeli Patent Application No. 243686, filed 19 Jan. 2016, entitled "ENHANCING EPITHELIAL INTEGRITY BY A SEQUENCE OF MAGNETIC PULSES." The contents of these applications are incorporated herein by reference in their entirety.

FIELD OF THE INVENTION

The present invention relates to systems, devices and methods for the treatment of eye conditions.

BACKGROUND OF THE INVENTION

Epithelial surfaces of the body provide a mechanical barrier against potentially harmful influences from outside and belong to key components of the body's defense. Epithelial intercellular adhesion and the intracellular junctions are regulated by various factors and are fundamental to the formation of the epithelial protective barrier. The transfer of substances across the epithelium occurs either through the cells (transcellular transfer) or through the intercellular space between the cells (paracellular transfer), the latter may include transient breaks in the epithelial barrier, but many details in the epithelium function remain unknown. The epithelium status affects, among others, susceptibility to viral, bacterial, and fungal infections and to other pathologies. In case of cornea, for example, disruption of the epithelial barrier can lead to discomfort, pain, acute injury, vision loss, and to various chronic syndromes. The integrity of epithelial layers may be determined by several methods, for example by paracellular flux of fluorescent molecules.

Methods for improving epithelial integrity were suggested for specialized epithelial tissues such as alveolar tissue; for example, effects of macrolides on epithelial barrier function was considered in treating lung diseases [Y. S. López-Boado and B. K.: Current Opinion in Pharmacology 8 (2008) 286-291]. However, a general method for affecting the epithelial integrity is not available. It is therefore an object of the invention to provide a method of enhancing the integrity of an epithelial layer.

Particularly, the corneal epithelium is the principal barrier to the penetration of noxious substances into the anterior chamber, and assists in protecting the cornea by maintaining normal hydration and retaining ocular surface integrity. This diffusion barrier blocks the penetration of polarized substances such as water or ions as well as macromolecules and cells, and represents 50% of the total diffusion barrier of the healthy cornea. The corneal epithelium consists of five cell layers of stratified squamous nonkeratinized cells and an underlying basal layer. The barrier function depends on epithelial cell tight junctions, the assembly of which is regulated by intra and extra-cellular calcium. Even minor lesions of the corneal surface, too small to be recognized in the daily clinical setting, may result in impairment of the corneal epithelial barrier function that can be quantified in vivo by means of objective fluorophotometry. Corneal epithelial dysfunction may render the cornea susceptible to a variety of pathologies, including potentially hazardous bacterial or fungal infections. Several systemic and ocular conditions are associated with reduced barrier function of the cornea, thus increasing vulnerability to the above complications. An example is seen in the diabetic population, which suffers from a fivefold decrease in corneal barrier function. Aging is also associated with reduced epithelial barrier function, with an exponential increase in epithelial permeability with advanced age. Another example is the common condition called dry eye (keratoconjunctivitis sicca or keratitis sicca), which results in corneal epithelial lesions and increased permeation.

Dry eye syndrome (DES) affects over 25 million people in USA and is one of the main reasons people visit their eye doctor. In its mildest forms DES causes bothersome symptoms of ocular discomfort, fatigue, and visual disturbance that interfere with quality of life. In its more severe form, DES causes chronic pain and fluctuating vision. Although DES is highly prevalent and costs billions of dollars to manage, current treatments have largely been inadequate, making it a frustrating condition, both for physicians and patients. In dry eye, the tear film, which normally spreads over the front of the eye and assists in protecting the cornea by maintaining normal hydration and retaining ocular surface integrity, becomes unstable and dry spots develop on the surface of the eye. In those dry spots the surface epithelial cells die and are sloughed off, while perturbing the corneal barrier function and increasing the risk of eye infection. The nerve ends in those dry spots become unprotected, which leads to discomfort and pain. Many types of eye drops have been offered to improve disturbed corneal epithelial surface but their efficiency is limited, and non-compliance is still a widespread problem. A possibility to decrease corneal permeability could help millions of patients suffering from mild or severe corneal barrier defects. It has been shown that exposure to magnetic fields modulates vascular tone and permeability of some tissues [see, for example, Okano H. et al.: Bioelectromagnetics 20(3) (1999) 161-71]. Alternating magnetic field was shown to reduce the permeability of cornea [WO 2014/181327]. It is therefore another object of the invention to provide a method for enhancing the epithelial integrity of the cornea by employing magnetic signals.

It is a further object of the invention to provide a device for treating eye disorders, comprising noninvasively reducing the corneal permeability by the use of magnetic field.

It is also an object of the invention to provide a noninvasive magnetic system for enhancing the corneal integrity.

It is a still further object of the invention to provide a magnetic system for enhancing the barrier function of an epithelial layer.

Other objects and advantages of present invention will appear as description proceeds.

SUMMARY OF THE INVENTION

The invention relates to a magnetic device for treating an epithelial layer, comprising a generator of magnetic pulses having a magnitude of up to 3 T, usually between 0.05 T and 2 T, in the vicinity of said layer, or at a distance of up to 10 cm from said generator, and a duration of from 50 µs to 2000 µs, such as between 200 µs and 2000 µs, wherein said magnitude increases during said pulse at a rate of change of at least 200 T/s in the absolute value. In a preferred embodiment of the invention, said rate of change is at least 1000 T/s in the absolute value, such as at least 2,000 T/s. Said rate of change may reach up to 100,000 T/s, but in many cases it will be up to 25,000 T/s in the absolute value. In one embodiment, the device produces said pulses at a rate of at least 1 pulse/s, usually up to 200 pulse/s, such as between 5 and 150 pulse/s, for example between 10 and 100 pulse/s. Said device advantageously enhances the integrity of said epithelial layer.

The invention provides a method of noninvasively treating a condition associated with reduced integrity or increased permeability of an epithelial layer or epithelial tissue, comprising creating near the epithelial layer magnetic pulses having a magnitude of up to 3 T and a duration of from 50 μs and 2000 μs, wherein said magnitude increases during said pulse at a rate of change of at least 200 T/s in the absolute value, preferably at least 2,000 T/s in the absolute value, usually up to 20,000 T/s in the absolute value, wherein the rate of the pulses is at least 1 pulse/s, usually up to 200 pulse/s, for example between 5 and 150 pulse/s, such as 20-100 pulses/s. In one embodiment of the invention, equal pulses form a series of between 0.5 and 20 s, followed by a signal break, which "train" may be repeated according to the needs. In one embodiment, the pulses form series of 20-200 pulses within an interval of 1 to 10 s, followed by a break without a magnetic signal of about 1 to 100 s, which train may be repeated, for example 100 times. When using expression "in the absolute value" in relation to the magnetic field, the intention is that the direction is disregarded both in regard to the strength of the field and its time change.

In one aspect of the invention, provided is a magnetic device for treating a cornea, comprising a generator of magnetic pulses having a magnitude of up to 3 T in the vicinity of said cornea, or at a distance of up to 10 cm from said generator, and a duration of from 50 μs and 2000 μs, wherein said magnitude increases during said pulse at a rate of change of at least 200 T/s in the absolute value. In a preferred embodiment of the invention, said rate of change is at least 2,000 T/s in the absolute value. Said rate of change may usually reach up to 20,000 T/s in the absolute value. In one embodiment, the device produces said pulses at a rate of at least 1 pulse/s, usually up to 200 pulse/s, preferably between 5 and 150 pulse/s, for example between 10 and 100 pulse/s. Said device advantageously enhances the integrity of said epithelial layer. In another aspect, the invention provides a method of noninvasively treating cornea, comprising creating near the cornea magnetic pulses having a magnitude of up to 3 T and a duration of from 50 μs and 2000 μs, wherein said magnitude increases during said pulse at a rate of change of at least 200 T/s in the absolute value, preferably at least 2,000 T/s in the absolute value, usually up to 20,000 T/s in the absolute value, wherein the rate of the pulses is up to 200 pulse/s, for example 20-100 pulse/s. In one embodiment of the invention, as can be seen with reference to FIG. 1, the magnetic field is perpendicular to the surface of the cornea; in another embodiment, the component of the magnetic field that is perpendicular to the surface of the cornea is at least 0.1 T. The term epithelial layer is used in the same sense as epithelial tissue or epithelium; it is known that epithelial and endothelial tissues line the cavities and surfaces of the organs and vessels in the animal body, being arranged in layers, which layers comprise certain surface and certain orientation. Generally, the component of the magnetic field that is perpendicular to the surface of a biological cellular layer is preferably at least 0.1 T. In an important embodiment of the invention, the device and method comprising the described magnetic signals are employed in treating biological cellular layers, particularly layers whose barrier function or integrity is compromised or whose integrity must be enhanced, or whose permeability must be reduced in order to achieve desired therapeutic goals; said layers may comprise any type of tissue; in a preferred embodiment, said layer comprises endothelium and epithelium, as well as adjacent tissue layers. It is important that the magnetic field component which is perpendicular to the surface of the treated layer be at least 0.1 T, in case of essentially non-planar layers, such as small curved layers, the generated field must provide a field whose perpendicular component to any part of the treated layer will reach at least 0.1 T, which may be attained either by moving the generator in desired directions or by applying a field which continually or discontinuously changes direction during the treatment.

In a preferred embodiment of the invention, provided is a device and method for treating a condition or a disease which requires increasing epithelial integrity or reducing epithelial permeability of an organ, comprising creating magnetic pulses having a magnitude of up to 3 T, for example between 0.1 T and 2 T, such as about 1 T, in the vicinity of said organ, said pulse having a duration of from 50 μs and 2000 μs, for example between 100 and 2000 μs, such as about 300 μs, wherein said magnitude increases during said pulse at a rate of change of at least 200 T/s in the absolute value, for example at least 1000 T/s, such as between 1000 T/s and 20,000 T/s in the absolute value, wherein the pulse rate is up to 500 pulse/s, for example between 10 and 200 pulse/s, such as between 15 and 100 pulse/s, for example about 20 pulse/s. Said device advantageously enhances the integrity of said epithelium or reduces its permeability.

In a preferred embodiment of the invention, provided is a magnetic device and system for treating the eyes, comprising a generator of a changing magnetic field, applied to said eyes or eye, the field having a strength of from 0.05 to 2 T at a distance of up to 10 cm from the generator, or in the vicinity of said eyes or eye, preferably between 0.1 and 1.5 T in the direction perpendicular to the surface of the treated cornea; the field having a rate of from 5 pulse/s to 500 pulse/s, and preferably being generated in pulses having a duration of from 50 μs and 2000 μs, for example in trains of from 10 to 100 pulse/s in a period of 0.5 s to 20 s, followed by a silent interval, for example from 1 to 20 s long, wherein the pulse may have a sinusoidal shape, possibly decaying, or other shape, of any direction. A magnetic device for treating the eyes according to one embodiment of the invention is configured to be worn by a subject in need of the treatment. The device for treating the eyes according to the invention may have a form similar to a virtual reality head-mounted display or to night vision goggles, it can also be a table-top device onto which the patient rests the chin and/or forehead. The important thing is that the magnetic field generator is placed at a well-regulated distance from the treated tissue.

The magnetic device according to the invention is advantageously employed in treating or preventing conditions selected from the group consisting of eye dryness, Sjögren's syndrome, keratitis sicca, corneal keratitis, corneal epithelial dysfunctions, reduced barrier function of the cornea associated with diabetes, conditions associated with increased corneal permeability due to ageing, minor lesions of the corneal surface, conditions associated with wearing contact lenses, reduced self-healing capabilities of the cornea, penetration of harmful agents to the eye from the contaminated environment, weakened anti-penetration system, cornea-associated inflammation, and corneal defects following ophthalmic surgical procedures such as LASIK procedure.

The invention provides a method of noninvasively treating an eye of a subject, comprising creating a changing magnetic field in the vicinity of the cornea of said eye, the field having a strength of from 0.05 to 3 T and comprising pulses having a duration of between 50 and 2000 μs. In a preferred embodiment of the invention the magnetic field exhibits a change of the magnitude of at least 200 T/s in the absolute value, usually between 2,000 and 20,000 T/s. In a preferred embodiment of the method according to the invention, an eye treatment aims at reducing the corneal permeability by applying the magnetic field, whereby protecting the eye against entrance of noxious agents or against loss of water, comprising magnetic pulse trains of 10-200 pulse/s during several seconds followed by several second intervals, which trains may be repeated, for example up to 100 times during one session; the sessions are repeated according to the achieved effects or according to the predetermined regimen. The method according to the invention comprises treating or preventing conditions selected from the group consisting of eye dryness, keratitis sicca, corneal keratitis, corneal epithelial dysfunctions, reduced barrier function of the cornea associated with diabetes, conditions associated with increased corneal permeability due to ageing, minor lesions of the corneal surface, conditions associated with wearing contact lenses, reduced self-healing capabilities of the cornea, penetration of harmful agents to the eye from the contaminated environment, weakened anti-penetration system, and cornea-associated inflammation.

BRIEF DESCRIPTION OF THE DRAWINGS

The principles and operation of the system, apparatus, and method according to the present invention may be better understood with reference to the drawings, and the following description, it being understood that these drawings are given for illustrative purposes only and are not meant to be limiting, wherein:

FIG. 3 is a text book drawing showing tissues, and in particular tissues around the eye, with a depiction of neurons that may be effected by a treatment as described herein, as described in research conducted using elements of the present invention; and FIG. 4 is a diagram describing test results showing a lasting effect following a (single) treatment, for example, within up to 3 months, even though multiple treatments may be performed, as described research conducted using elements of the present invention.

DETAILED DESCRIPTION OF THE INVENTION

It has now been found that certain types of magnetic field are particularly efficient in reducing the permeability of the cornea and enhancing the corneal integrity. In some embodiments, a magnetic signal may be provided in pulses comprising the field strength of between 0.2 T to 2 T, and with an amplitude change of between 7,000 to 15,000 T/s, to substantially reduce the permeability of a compromised cornea, for example when repetitively applied for between 200-500 micro seconds pulses at a rate of between 15 to 50 pulse per second. In one example, as applied to a rabbit cornea, a magnetic signal provided in pulses comprising the field strength of about 0.2 T and the amplitude change of about 13,000 T/s substantially reduced the permeability of a compromised rabbit cornea toward fluorescein, for example when repetitively applied for around 100 ms at a rate of 20 pulse/s.

Figure 1:
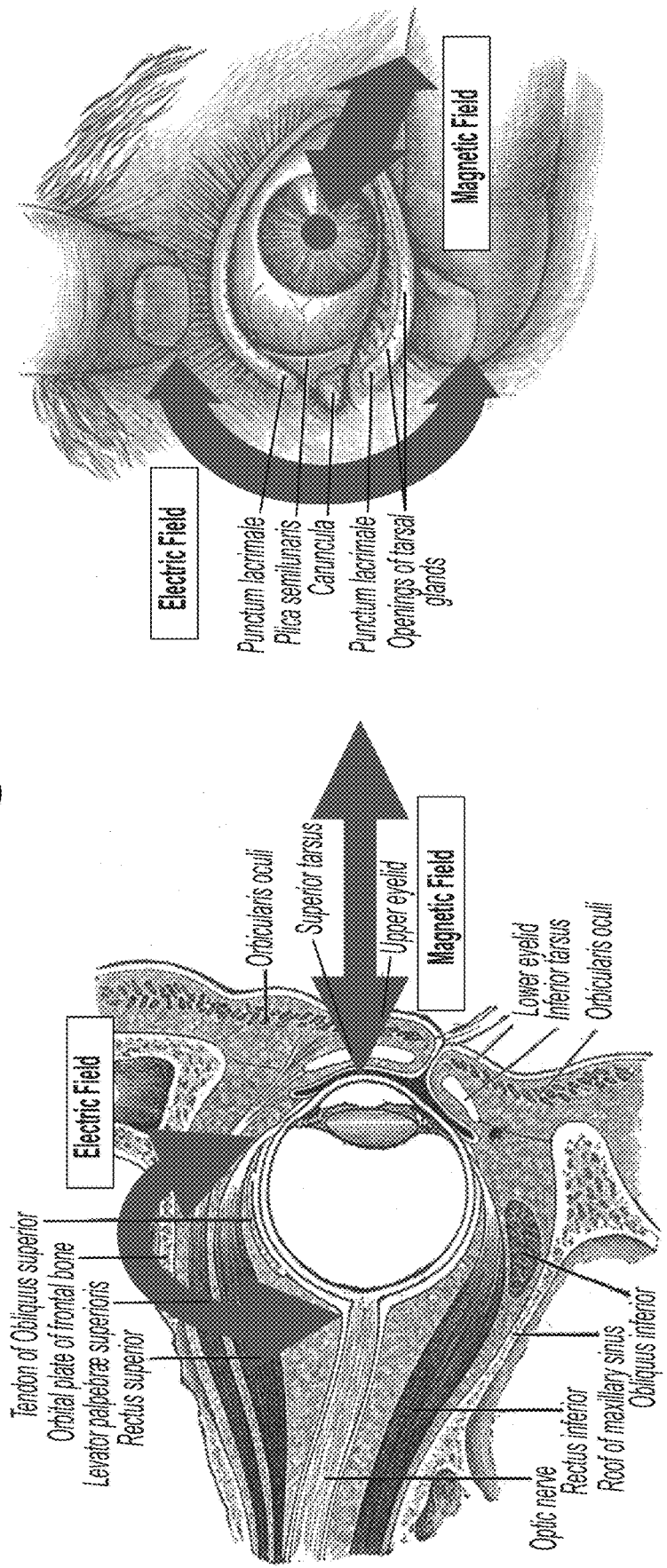
FIG. 1 is a text book drawing that shows an imposed depiction of a perpendicular magnetic field and a circular electric field around the eye, as shown in research conducted using elements of the present invention.
Figure 2:
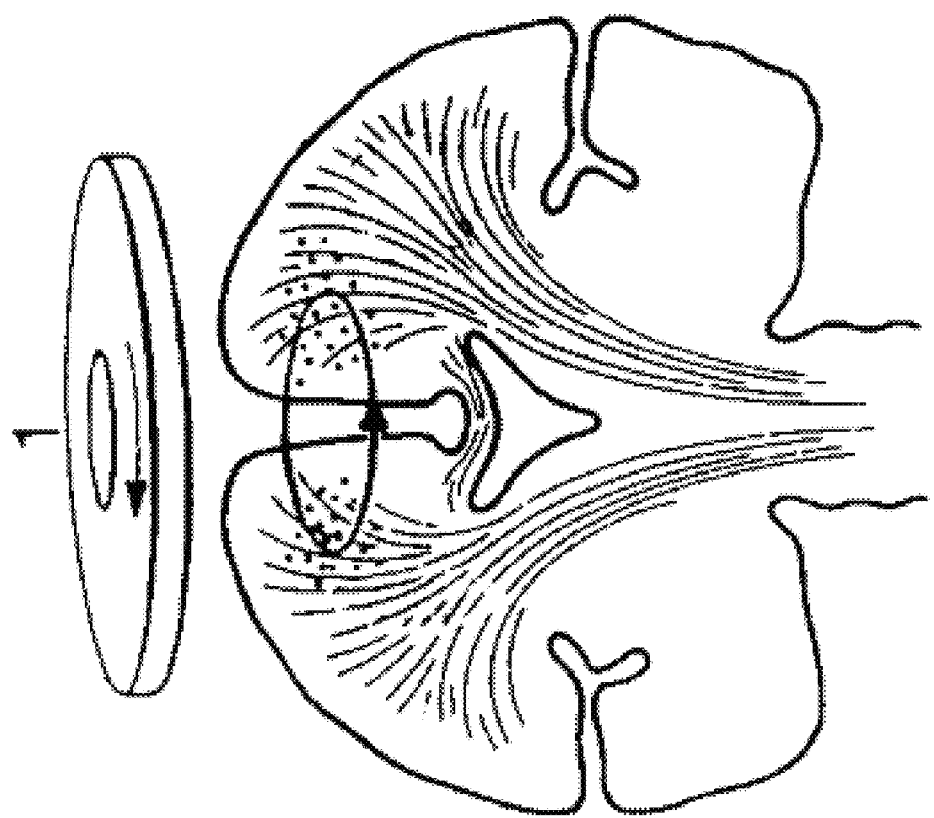
FIG. 2 is a prior art (P. J. Maccabee Et. Al., page 44, FIG. 6) diagram depicting a magnetic coil 1 with an arrow showing direction of electric current, and a coronal cross section of the brain showing the circular direction of an induced electric field.

When employing a field of at least 0.1 T, changing with a rate of change of at least 200 T/s in the absolute value, various pulse-shaped signals may be employed. It is understood that changing magnetic field comprises an electric component (electromagnetic field), but for technical reasons, the magnetic component was regulated in the generators employed in the development work which resulted in the invention, and it is the magnetic component to which the description of the invention mainly relates. The alternating magnetic field can induce electric fields in tissues [P. J. Maccabee et al.: J. Clin. Neurophysiol. 8(1) (1991) 38-55], as described with reference to FIG. 2, it may affect cells growth, it may modulate vascular tone and permeability by modulating calcium channels in vascular smooth muscle cells [Okano H. et al.: Bioelectromagnetics 20(3) (1999) 161-71]. Determination of potential mechanisms involved in this physiological responses to magnetic field exposure is ongoing, and multiple and variable biological mechanisms have been suggested [see WO 2014/181327 of the same inventors]. The inventors believe that induced electrical fields and electrical currents, affecting various types of tissues, including neurons, as described with reference to FIG. 3, contribute to the overall effects, at least in case of corneal treatment. Both magnetic and electric components may affect the cellular function, for example in epithelium, by altering mechanisms associated with survival, proliferation, orientation, migration, differentiation, cell adhesion, protein phosphorylation, gene expression, metabolic state, RNA & micro RNA expression, and others. For example, in regard to the human cornea, it comprises several layers, such as corneal endothelium, Descemet's membrane, corneal stroma, Bowman's layer, and corneal epithelium, and in addition the human cornea is one of the most richly innervated structures in the body and is densely supplied by sensory and autonomic nerve fibers; the magnetic and electric stimulation of the mentioned tissues may contribute to the whole positive treatment effect.

The magnetic field employed in a system according to the present invention comprises electromagnetic field of which magnetic component near the treated tissue has a strength of between 0.05 and 3 T, such as at least 0.1 T, or at least 0.2 T, or at least 0.3 T, or at least 0.4 T, or at least 0.5 T. In this context, the strength of the magnetic field means the peak amplitude of the pulse. The magnetic field employed in a system, method, or device according to the present invention includes a strength near the treated tissue of about 0.1 T or 0.2 T or 0.3 T or 0.4 T or 0.5 T or 0.6 T or 0.7 T or 0.8 T or 0.9 T or 1 T or 1.2 T or 1.4 T or 1.6 T, wherein the field amplitude changes in the absolute value at a rate of change of at least 200 T/s. The term "about" before a value means the value ±10%; however, it is understood that all experimental values may vary within certain error, and a range of ±10% is usually assumed as such an error. Said strength may be considered in the vicinity of the epithelial tissue to be treated or near the field generator; the distance of the generator may be usually up to 15 cm, such as up to 10 cm, for example in case of treating cornea the distance may be similar to the distance of the eyeglasses from the eye surface, for example, between 0.5 cm to 3 cm. The magnetic field may be an alternating field, and preferably is a pulsed field having a rate between 5 to 500 pulse/s, such as 20 pulse/s. The field is preferably applied repetitively, comprising pulses preferably between 50 and 2000 μs long applied as trains in periods of 0.5 to 20 s separated by intervals, possibly of similar duration. The total treatment session time is usually between 1 and 60 minutes. In some embodiments, a treatment session takes up to 30 min, with various arrangements of pulses within the session, comprising a pulse rate of between 0 and 200 pulse/s; a session may include several different sections, for example comprising rates of 20, 0, 50, and 200 pulse/sec.

The invention provides, in one embodiment, a device for treating eye conditions associated with reduced corneal integrity, which can be worn by a person, in which a magnetic field generator is incorporated. The generator can generate a magnetic field of different parameters. The magnetic field reaches the eye. The decrease of the corneal permeability protects the cornea from physical damages, for example in persons suffering from eye dryness.

Certain magnetic stimulations decrease the permeability of the cornea, beneficially affecting persons suffering from eye dryness or persons wearing contact-lenses, who are afflicted with decreased lubrication of the eye, known to make the cornea more susceptible to different types of damages. It has been found by the inventors that repetitive magnetic stimulation reduces the corneal permeability as desired; the field preferably comprising changing magnetic field which has a strength of at least 0.1 T, preferably about 1 T or more, and which changes at a rate of change of at least 200 T/s, preferably more than 1000 T/s, preferably provided in pulses at a rate of 5-500 pulse/s, such as 10-100 pulse/s, for example 20 pulse/s; such field enhances the corneal integrity and so protects the eye from damages eventually caused by undesired entry of damaging agents from the environment and/or undesired exit of eye liquids.

This invention provides a device, a method, and a system for reducing the corneal permeability and enhancing corneal integrity by applying magnetic pulses comprising a strength of at least 0.1 T and a time change in the absolute value of at least 200 T/s, so assisting clinicians and pharmacologists challenged by eye disorders in which the corneal function is perturbed. The invention enables to treat or to prevent or to mitigate the conditions selected from the group consisting of eye dryness, keratitis sicca, corneal keratitis, corneal epithelial dysfunctions, reduced barrier function of the cornea associated with diabetes, conditions associated with increased corneal permeability due to ageing, minor lesions of the corneal surface, conditions associated with wearing contact lenses, reduced self-healing capabilities of the cornea, penetration of harmful agents to the eye from the contaminated environment, weakened anti-penetration system, and cornea-associated inflammation. The conditions to be handled by the device and method of the invention may be associated with items selected from the group consisting of keratitis caused be contact lenses, epidemic keratoconjunctivitis, aging of the cornea, epithelial corneal dystrophies, atopic keratoconjunctivitis, vernal keratoconjunctivitis, allograft corneal epithelial rejection, limbal chemical burn, epithelial keratitis—herpes simplex, epithelial keratitis—neurotropic, Sjogren's syndrome, tear production induced by anti-Parkinson agents or anti-spasmotic agents or antiulcer-agents or aqueous tear deficiency medication, staphylococcal belephritis, argon laser burns, Reiter syndrome, rheumatoid peripheral ulcerative keratitis, systemic diseases, and after ophthalmic procedures such as LASIK and others. The device and method of the invention may advantageously handle post-operative conditions which expose the cornea to susceptibility of dry eye such as any refractive type of surgery, other corneal surgeries, cataract surgeries and glaucoma surgeries, systemic diseases and conditions which may cause dry eye including diabetes autoimmune diseases, as well as the conditions associated with treatment including local drops which cause corneal epithelial damage or with systemic treatment which may cause dry eye.

In exemplifying some embodiments of the invention, ocular penetration of sodium-fluorescein in rabbit eyes following magnetic stimulation at different intensities was used. The model using rabbit eyes and sodium fluorescein was employed by the inventors due to the high ocular safety profile of the compound, its hydrophilic nature, and the fact that corneal staining by this fluorescent dye is the acceptable clinical measure for epithelial damage, as well as the ability to measure its concentration in the anterior chamber with good precision and reproducibility using a fluorometer. The baseline corneal permeability of this hydrophilic substance is very limited, due to the corneal barrier function. It is known that fluorescein does not penetrate or stain live corneal epithelial cells upon topical application, the corneal epithelial defects are readily stained as the dye diffuses between cells into the adjacent intercellular spaces and penetrates into the underlying corneal stroma. Rabbits were either non treated (sham) or treated with magnetic pulses of minimal strength and minimal amplitude time change one hour prior to fluorescein application. Corneal staining by fluorescein as well as fluorescence measurements of anterior chamber fluid were used to quantify the ocular penetration. In order to demonstrate the safety of the procedure, animals were tested for retinal function by electro-retinogram prior to the magnetic treatment, at 1 day, 1 week, 1 month, and 9 weeks following the treatment. Moreover, animals were examined by optical coherence tomography (OCT), histological analysis, and other methods for possible adverse effects on retinal structure.

The invention enables to enhance the corneal integrity. Ocular surface disease comprises numerous disorders affecting millions around the world, and is a problem encountered routinely in daily practice. A subgroup of these patients suffers from a chronic compromise of the corneal surface, which in turn may result in corneal scarring, infection, thinning and ultimately perforation. In this subgroup, the self-healing capabilities of the cornea are significantly impaired in comparison to normal corneas. A method for enhancing corneal integrity and reducing permeability may serve to help protect these compromised corneas, and may even facilitate accelerated healing. The invention enables to reduce the permeability in cornea subjected to magnetic stimulation, so safeguarding the ocular surface in these delicate situations. It was found that the best results were achieved with magnetic pulses of relatively strong field including relatively quick field amplitude changes, such as at least 0.1 T, for example about 0.2 T or 0.3 T or 0.4 T or 0.5 T or 0.6 T or 0.7 T or 0.8 T or 0.9 T or about 1 T, changing at a rate of change of at least 1000 T/s, such as at least 5,000 T/s or at least 10,000 T/s or at least 15,000 T/s, administered for example at a rate of at least 10 pulse/s, such as about 15 pulse/s or about 20 pulse/s or about 25 pulse/s. This was achieved with pulses of a duration of preferably between 100 and 2000 μs, such as between 150 and 1500 μs or between 200 and 1000 μs.

The term "strength" in regard to the magnetic field is used in the same sense as the term "intensity", intending the field magnitude measured in the units of tesla (T). The terms "amplitude time change", or "velocity of the field strength change", or "velocity of magnitude increase", or "rate of change" relate to the time derivative of the magnetic field magnitude, regardless the direction and the sign, and it can be obtained either by differentiating a known time signal shape (time development of the magnetic magnitude/ strength), or they can be roughly assessed from the pulse magnitude and duration, as experts will acknowledge. For example, a biphasic pulse having a duration of about 100 μs and a maximal intensity of about 0.2 T, will comprise a maximum rate of change of about 12,500 T/s [$0.2*2\pi/(100*10^{-6})$]; of course, the rate of change (dB/dt) goes through all the values from −12500 to +12500 during the pulse.

The system and device of the invention enable a noninvasive treatment by magnetic pulses which enhance the barrier function of a cellular layer such as of an epithelium. In a preferred embodiment, the system and device of the invention assist in protecting the cornea by retaining ocular surface integrity via reducing the corneal permeability. The magnetic treatment according to the invention protects epithelial barrier (function and structure), particularly it decreases corneal permeability, preferably in handling dry eye and conditions manifested by the dry eye syndrome, or in handling other conditions where corneal permeability is increased, including operations, diseases, trauma desiccation, and others. The treatment may reduce eye dehydration, pain, discomfort, and infection, and it may handle the situations when the barrier functions are compromised, such as in cases of reduced blinking.

The invention will be further described and illustrated in the following examples.

EXAMPLES

Method:

The application of magnetic pulses was found to protect corneal epithelium in a dry eye model in rabbits. To investigate the effect of the pulses on corneal epithelial permeability in a short-term dry eye model in rabbits, thirteen New Zealand white rabbits were used. One eye of each rabbit was treated with magnetic stimulation (Rapid2 stimulator, Magstim) at 20 pulse/s, the field strength of about 0.8 T, the treatment session of about 10 minutes. The other untreated eye served as a control. One hour later, rabbits were anesthetized and eyes were kept open for two hours to induce acute corneal desiccation. To evaluate corneal barrier, five microliters of sodium fluorescein (10%) were instilled on rabbit corneas. Extent of fluorescein corneal staining was evaluated using IMAGE J. Fluorescein penetration through the corneal barrier was assessed by determining fluorescein concentration in a 100 microliter sample withdrawn from the anterior chamber 1 hour following fluorescein installation. To determine duration of the therapeutic effect, five rabbits underwent acute corneal desiccation once a week for five weeks, and monitored for fluorescence in corneal staining and penetration to the anterior chamber. Histopathology and optical coherence tomography (OCT) were used to evaluate the safety of the treatment.

Results:

Compared with untreated control eyes, the magnetic-pulse treated eyes showed a significant decrease in fluorescein concentration in the anterior chamber (147 ng/ml [SE=19] vs 54 ng/ml [SE=9], p=0.00005) and in percentage of corneal surface stained with fluorescein (2% [SE=4.5] versus 17.4%[SE=3.4], p=0.001, wherein SE is standard error). As can be seen with reference to FIG. 4, Therapeutic effect was maintained for 3 months, with significantly lower fluorescein corneal staining in eyes treated with RMS versus control non-treated eyes. OCT and histopathology analysis revealed no gross or microscopic pathological changes in any of the eyes that underwent treatment or the contralateral eyes.

Conclusions:

In a preclinical study, the inventors demonstrated that treatment with the magnetic pulses protected the epithelial layer in the dry spots, preventing loss of the epithelial cells and maintaining the function of the corneal barrier under extreme desiccation conditions. One short (12 minutes) magnetic treatment supported corneal barrier integrity under acute dry eye conditions for at least 3 months. The treatment was safe; there was no damage in any ocular tissue as determined by imaging and pathological analyses. These findings demonstrate that the treatment according to the invention may present a novel means not only for protecting the corneal epithelium from desiccation in the patients with dry eye, but also for protecting a cellular barrier such as an epithelial barrier in general.

While the invention has been described using some specific examples, many modifications and variations are possible. It is therefore understood that the invention is not intended to be limited in any way, other than by the scope of the appended claims.

The invention claimed is:

1. A system for applying electromagnetic stimulation to a periocular region of an eye for treating dry eye syndrome, the system comprising:
    an electromagnetic field generator arranged to provide a time varying electromagnetic field having:
        an output pulse duration of between 200-400 microseconds;
        a rate of change of between 10K and 20K Tesla per second; and
        a pulse rate of 1-50 Hz; and
    a positioner configured for locating an output of said electromagnetic field generator at said periocular region of the eye.

2. The system according to claim 1 and wherein said electromagnetic field generator is operative to generate a predetermined sequence of pulses forming a treatment session.

3. The system according to claim 2 and wherein said treatment session comprises time intervals during which a series of pulses are generated and time intervals during which no series of pulses are generated.

4. A method for treating dry eye syndrome by applying electromagnetic stimulation to a periocular region of an eye, the method comprising:
    generating a time varying electromagnetic field, said time varying electromagnetic field having:
        an output pulse duration of between 200-400 microseconds;
        a rate of change of between 10K and 20K Tesla per second; and
        a pulse rate of 1-50 Hz; and
    locating said time varying electromagnetic field at said periocular region of the eye.

5. The method according to claim 4 and wherein said generating said time varying electromagnetic field comprises providing an electromagnetic field generator.

6. The method according to claim 5 and wherein said providing said electromagnetic field generator comprises providing a wearable device.

7. The method according to claim 6 and wherein said providing said wearable device comprises providing a head mountable device.

8. The method according to claim 5 and wherein said locating comprises locating said electromagnetic field generator at a distance of less than 10 cm from said periocular region of the eye.

9. The method according to claim 4 and wherein said generating a time varying electromagnetic field comprises generating a predetermined sequence of pulses forming a treatment session.

10. The method according to claim 9 and wherein said treatment session comprises time intervals during which a series of pulses are generated and time intervals during which no series of pulses are generated.

* * * * *